(12) United States Patent
De Vos

(10) Patent No.: US 8,914,116 B2
(45) Date of Patent: Dec. 16, 2014

(54) NOSE STIMULATOR FOR PRODUCING A STIMULATION SIGNAL TO A NOSE

(75) Inventor: Gerrit Johannis De Vos, 's-Heerhendrikskinderen (NL)

(73) Assignee: NasoPhlex B.V. (NL)

( * ) Notice: Subject to any disclaimer, the term of this patent is extended or adjusted under 35 U.S.C. 154(b) by 426 days.

(21) Appl. No.: 13/000,336

(22) PCT Filed: Jun. 18, 2009

(86) PCT No.: PCT/NL2009/050357
§ 371 (c)(1),
(2), (4) Date: Mar. 11, 2011

(87) PCT Pub. No.: WO2009/154457
PCT Pub. Date: Dec. 23, 2009

(65) Prior Publication Data
US 2011/0313481 A1 Dec. 22, 2011

(30) Foreign Application Priority Data

Jun. 18, 2008 (NL) .................................... 2001697

(51) Int. Cl.
| | | |
|---|---|---|
| *A61N 1/04* | (2006.01) | |
| *A61N 1/372* | (2006.01) | |
| *A61N 1/05* | (2006.01) | |
| *A61H 39/00* | (2006.01) | |
| *A61N 1/36* | (2006.01) | |
| *A61B 5/00* | (2006.01) | |
| *A61B 7/00* | (2006.01) | |

(52) U.S. Cl.
CPC .............. *A61N 1/3601* (2013.01); *A61B 5/7217* (2013.01); *A61H 2230/40* (2013.01); *A61H 2201/1604* (2013.01); *A61N 1/0546* (2013.01); *A61H 2205/023* (2013.01); *A61H 2201/165* (2013.01); *A61B 7/003* (2013.01); *A61B 5/4818* (2013.01); *A61H 39/002* (2013.01); *A61H 2201/1607* (2013.01); *A61H 2205/022* (2013.01); *A61H 2230/06* (2013.01)
USPC .............................. 607/45; 607/135; 607/140

(58) Field of Classification Search
CPC . A61N 1/0546; A61N 1/3601; A61N 1/3611; A61N 2005/0607; A61B 5/08; A61B 5/4818; A61H 2205/022; A61H 2205/023
USPC ........................................... 607/42, 135, 140
See application file for complete search history.

(56) References Cited

U.S. PATENT DOCUMENTS

| 4,969,468 A | 11/1990 | Byers et al. |
|---|---|---|
| 5,178,156 A * | 1/1993 | Takishima et al. ............ 600/537 |

(Continued)

FOREIGN PATENT DOCUMENTS

| CA | 2 507 142 | 10/2006 |
|---|---|---|
| EP | 0 404 427 | 12/1990 |

(Continued)

OTHER PUBLICATIONS

Benacka, R. et al., "The sniff-like aspiration reflex evoked by electrical stimulation of the nasopharynx," Respiration Physiology, Amsterdam, NL, vol. 102, No. 2-3, Dec. 1, 1995, pp. 163-174.

(Continued)

*Primary Examiner* — Tammie K Heller
(74) *Attorney, Agent, or Firm* — Meyer IP Law Group

(57) ABSTRACT

An electronic stimulation system has a casing; electronics inside the casing a first detector arranged to sense whether a human being is breathing or not, a stimulation device arranged to receive a control signal from said electronics and to provide stimuli to a nasal philtre or a human nasopharynx. The electronics generate the control signal in dependence on the breathing signal and the system has a holding device for attaching the stimulation device to the nose.

19 Claims, 8 Drawing Sheets

(56) References Cited

U.S. PATENT DOCUMENTS

| | | | |
|---|---|---|---|
| 5,335,657 | A | 8/1994 | Terry, Jr. et al. |
| 5,514,175 | A | 5/1996 | Kim et al. |
| 5,571,148 | A | 11/1996 | Loeb et al. |
| 5,891,185 | A | 4/1999 | Freed et al. |
| 5,957,956 | A | 9/1999 | Kroll et al. |
| 6,368,287 | B1 | 4/2002 | Hadas |
| 6,603,654 | B2 | 8/2003 | Rorvick et al. |
| 6,928,324 | B2 * | 8/2005 | Park et al. ............ 607/20 |
| 2003/0100930 | A1 | 5/2003 | Cohen et al. |
| 2003/0139781 | A1 | 7/2003 | Bradley |
| 2003/0199945 | A1 | 10/2003 | Ciulla |
| 2004/0176673 | A1 | 9/2004 | Wahlstrand |
| 2004/0210261 | A1 | 10/2004 | King et al. |
| 2004/0215236 | A1 | 10/2004 | Lattner et al. |
| 2004/0243205 | A1 | 12/2004 | Keravel et al. |
| 2005/0159790 | A1 | 7/2005 | Shalev |
| 2006/0020299 | A1 | 1/2006 | Shalev |
| 2006/0064139 | A1 | 3/2006 | Chung et al. |
| 2006/0149319 | A1 | 7/2006 | Kuo et al. |
| 2006/0173259 | A1 | 8/2006 | Flaherty et al. |
| 2006/0206162 | A1 | 9/2006 | Wahlstrand et al. |
| 2006/0217779 | A1 | 9/2006 | Ransbury et al. |
| 2007/0088404 | A1 | 4/2007 | Wyler et al. |
| 2007/0128420 | A1 | 6/2007 | Maghribi |
| 2007/0250145 | A1 | 10/2007 | Kraus et al. |
| 2007/0255379 | A1 | 11/2007 | Williams et al. |
| 2007/0255531 | A1 | 11/2007 | Drew |
| 2008/0103545 | A1 | 5/2008 | Bolea et al. |
| 2009/0240296 | A1 | 9/2009 | Zeijlemaker et al. |

FOREIGN PATENT DOCUMENTS

| | | |
|---|---|---|
| EP | 1 790 380 | 5/2007 |
| EP | 1 825 880 | 8/2007 |
| WO | 00/66215 | 11/2000 |
| WO | 2004/049937 | 6/2004 |
| WO | 2006/108630 | 10/2006 |
| WO | 2007/003019 | 1/2007 |
| WO | 2007/146213 | 12/2007 |
| WO | 2007147046 | 12/2007 |
| WO | 2008072948 | 6/2008 |
| WO | 2008/080062 | 7/2008 |
| WO | 2008/157435 | 12/2008 |

OTHER PUBLICATIONS

Janssens, L. et al., "Respiratory and cardiac arrest under general anaesthesia: treatment by acupuncture of the nasal philtrum," Abstract, MEDLINE, Jan. 1, 1900, 1 page.

Wang et al., Clinical Observation on Effect of Auricular Acupoint Pressing in Treating Sleep Apnea Syndrome, Medline, Jan. 1, 1990, 1 page.

Tomori et al., Hypoxic Apnoea Induced By N2 Inhalation Can Be Reversed By the Aspiration Reflex in Anaesthetized Cats, Respiratory Medicine, Bailliere Tindall, London, GB, vol. 85, Jan. 1, 1991, pp. 61-65.

Tomori, et al., Reflex reversal of apnoeic episodes by electrical stimulation of upper airway in cats, Respiration Physiology, Dec. 1, 1995, pp. 175-185, vol. 102, No. 2-3. Relevant Passages: Abstract; p. 176, right-hand column, paragraph 2; Methods—p. 184, right-hand column, last paragraph; Figures 1-4.

Tomori, et al., Mechanisms and clinicophysiological implications of the sniff-and gasp-like aspiration reflex, Respiration Physiology, Oct. 1, 1998, pp. 83-98, vol. 114, No. 1. Relevant Passages: Abstract; p. 85, right-hand column, paragraph 2; p. 88, right-hand column, last paragraph; p. 92, left-hand column, last paragraph—p. 93, right-hand column, last paragraph; Figure 1.

Yu, et al., Mechanisms of effects of electrical stimulation of "Renzhong" (Du 26) on phrenic discharge in rabbits, Journal of West China University of Medical Sciences, Dec. 1989, pp. 384-388, vol. 20, No. 4. Relevant Passages: p. 387, left-hand column, last paragraph—p. 3888, right-hand column, paragraph 1.

Changa, et al., Decrease of anesthetics activity by electroacupuncture on Jen-Chung point in rabbits, Neuroscience Letters, Dec. 1, 1995, pp. 93-96, vol. 202, No. 1-2. Relevant Passage: Abstract.

Hsu, et al., Shock resuscitation with acupuncture: case report, Emergency Medicine Journal, Mar. 1, 2006, 2 pages, vol. 23, No. 3. Relevant Passage: The whole document.

Oleson, et al., Electroacupuncture and auricular electrical stimulation, IEEE Engineering in Medicine and Biology Magazine, Dec. 1, 1983, pp. 22-26, vol. 2, No. 4, IEEE Service Center, Pisacataway, NJ, US. Relevant Passage: The whole document.

Miller, Oral and pharyngeal reflexes in the mammalian nervous system: their diverse range in complexity and the pivotal role of the tongue, Critical Reviews in Oral Biology & Medicine, Sep. 1, 2002, pp. 409-425, vol. 13, No. 5. Relevant Passages: Paragraphs [0095]-[0109], [0116]-[0131]; Figures 1-3, 7, 8.

* cited by examiner

US 8,914,116 B2

NOSE STIMULATOR FOR PRODUCING A STIMULATION SIGNAL TO A NOSE

FIELD OF THE INVENTION

The invention relates to an electronic system for producing a stimulation signal to a nose or an area close to the nose, e.g., to acupuncture point GV26 of the nasal philtre. The area is chosen such that the stimulation signal will induce an aspiration reflex in human beings.

BACKGROUND OF THE INVENTION

The brainstem contains a number of central mechanisms regulating a number of vital physiological functions. Disorders in the regulation of the cardio-pulmonary system can result in a number of pathological conditions some of which may be potentially life threatening.

People suffering from sleep apnoea have cardio-pulmonary disorders manifesting with breathing irregularities and even frequent stops of breathing (apnoea), particularly during sleep, but also during the day. The apnoeic episodes during the day-time are less dangerous, because they can be self-managed by conscious actions, apnoeas during the night are more dangerous. Patients can feel very sick in everyday life, due to oxygen deprivation. During episodes of apnoea, blood pressure can collapse and subsequently the heart may stop its function, resulting in inadequate brain perfusion, loss of consciousness and even sudden death. At least 4% of the adult population in developed countries suffers from sleep apnoea.

There are several types of apnoea. One type, central apnoea, involves a dysfunction of the respiratory muscles (including the diaphragm) for lack of command from the respiratory centre in the brainstem. This is the type occurring in approximately 10 percent of the cases. Another type, obstructive apnoea, occurs in 80% of cases, when in spite of respiratory movements there is no supply of air to the lungs, due to collapse of the upper airways. The third type, a mixed apnoea, occurs in the rest of the patients.

It is known, that apnoea can be counteracted by stimulation of the patient in various ways. In infants shaking is usually enough to arouse the baby from sleep and restart the process of automatic breathing and even provoke gasps, which induces resuscitation from asphyxia. Adults suffering from sleep apnoea now sleep with a mask, tightly connected to the facial contours, so a slight over-pressure of air from a device can continuously be applied (Continuous Positive Airway Pressure-CPAP). This keeps the airways open and allows air supply by spontaneous breathing. In any case these patients have to sleep attached to their breathing apparatus, limiting their freedom of movement during sleep. For patients with sleep apnoea travelling means carrying the breathing apparatus with them. For patients suffering from central sleep apnoea or mixed type sleep apnoea, treatment with CPAP is showing limited success. Modulating the air pressure (BI-PAP) offers only a lightly better success rate.

Research in cats has shown that breathing can be stopped by inhalation of anoxic mixtures for over 1 minute, with subsequently a severe drop in blood pressure and heart rate. Mechanical or electrical stimulation of the nasopharynx can induce a sniff- and gasp-like "aspiration reflex" (Tomori and Widdicombe, 1969, Beňačka & Tomori, 1995, Tomori et al. 1995, 1998, 2000). Due to resuscitation effects, the blood pressure returns to normal, heart rhythm normalizes, respiration and neuro-behavioral functions return to normal. The anesthetized cat seems to be in good condition, even after as long as three minutes without adequate blood pressure, heart rate and breathing. This experiment can be repeated over 10 times on the same cat, without any noticeable negative consequences.

Provocation of such an aspiration reflex has been indicated as a possible means for interruption of apnoea in cats (Tomori et al., 1991, 1995, Beňačka & Tomori, 1995, Jakus et al., 2004). Alternatively, similar resuscitation may be induced by (electro)-acupuncture, (electro)-acupressure or mechanical stimulation of the nasal philtre in cats, inducing spasmodic inspiration (Beňačka & Tomori, 1997).

PCT/NL2006/000599, which has not been published prior to the priority date of the present invention, describes the surprising discovery that a resuscitating stimulation of the brainstem with an induced aspiration reflex in order to obtain resuscitating physiological effects also works in human beings. That document also describes some devices designed for treating apnoea and related cardio-respiratory syndromes in humans via activation of the respiratory centre of the brainstem followed by an induced aspiration reflex.

PCT/NL2006/000599 describes a nose stimulator in general terms which may be designed to electrically or mechanically stimulate acupuncture point GV26 of the nasal philtre. This could be provided by an apparatus, attached under the patients nose, to monitor breathing by detecting airflow by a flowmeter and to stimulate acupuncture point GV26 under the nose during an apnoeic episode.

Janssens L., et al., Respiratory and cardiac arrest under general anaesthesia: treatment by acupuncture of the nasal philtre, The Veterinary record, 22 Sep. 1979, report that in some cases of anaesthetic apnoea with concurrent cardiac arrest and absence of vital signs in dogs and cats, needling of the nasal philtre point VG26 showed a revival rate of 43 percent. No such experiments on humans are known to the inventor of the present invention. Moreover, it is observed that successful experiments on dogs and cats is no guarantee at all for similar successful experiments on human beings.

SUMMARY OF THE INVENTION

The object of the present invention is to provide a nose stimulation device that can be used to generate a stimulus to a nose.

To that end, the invention provides a nose stimulator as claimed in claim 1.

The advantage of such an apparatus is that it can be easily attached to a human face without hindering the user too much.

BRIEF DESCRIPTION OF THE DRAWINGS

The invention will be explained in detail with reference to some drawings that are only intended to show embodiments of the invention and not to limit the scope. The scope of the invention is defined in the annexed claims and by its technical equivalents.

DESCRIPTION OF EMBODIMENTS

Figure 1:
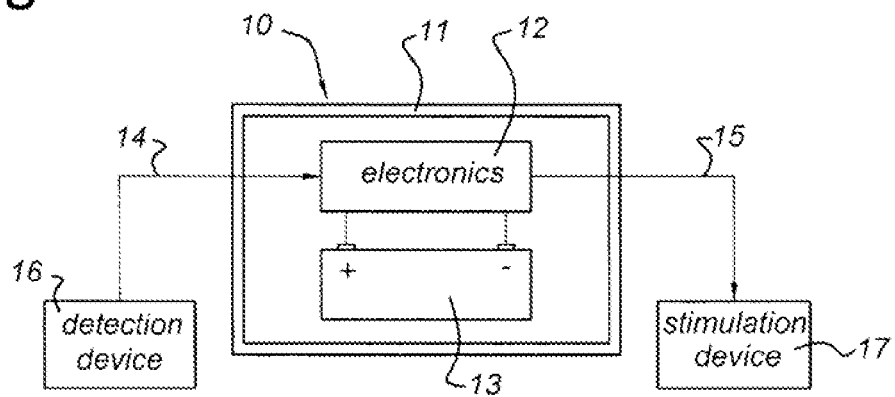
FIG. 1 shows a schematic block diagram of an electronic system according to the invention.

The present invention, among others, relates to devices suitable for inducing autoresuscitation in a subject in need thereof. The term autoresuscitation should be understood to comprise resuscitation by activation of natural compensatory mechanisms of the human organism via inducing a sniff- and/or gasp-like aspiration reflex, or its alternative forms in various species, similar to that provided by means of spontaneous gasping autoresuscitation observed in non-human animals and human infants (Sridhar et al., 2003; Xie et al., 2004). When referring to induction of autoresuscitation in this specification the term resuscitation may be used. Subjects that may benefit from induction of autoresuscitation are subjects suffering from and/or having a predisposition for functional disorders, such as hyper and hypo-function of the: a) respiratory system, b) cardiovascular system, c) neurobehavioral changes and d) psychiatric disorders. These include one or more of apnoea, transient ischemic attacks (TIA), bronchospasm also in asthmatics, laryngospasm, hiccup, tremor associated with Parkinson's disease, epileptic seizure, absence type epilepsy, migraine, hypotension, syncope, haemorhagic shock (loss of blood), alternating hemiplegia, Alzheimers disease, depression, anorexia nervosa, bulimia, autism, psychiatric disorders, sleep paralysis, insomnia, comatose states.

It is believed that the "aspiration reflex", via strong activation of the inspiratory centre, causes the controlling functions of the brainstem to be reset, similar to activation of brainstem centres during autoresuscitation induced by gasping. In rapid and strong inspiratory efforts during a gasp or a provoked aspiration reflex, activation of the inspiratory centre in the brainstem resets the failing centres of other vital functions, including the centres controlling cardiac activity, blood pressure, as well as various neuropsychic and somato-motor functions.

As indicated in PCT/NL2006/000599, without wishing to be bound by any theory, it is believed that inducing the aspiration reflex may be helpful in relation to the following 5 groups of disorders of the human body.

1. In patients with apnoea and hypopnoea caused by transient inactivity of the inspiratory neurons in the brainstem, induction of the aspiration reflex can reverse the apnoea or hypopnoea and restore spontaneous breathing. In patients with obstructive apnoea, the stimulation of the inspiratory centre in the brainstem may reverse the closure of the airways and restore normal breathing.
2. In patients with Transient Ischemic Attack (TIA), syncope, hypotension, migraine and hemorrhagic shock the aspiration reflex activates, via the respiratory centre, the brainstem vasomotor centre to evoke periferal vasoconstriction and vaso-dilatation in the brain and heart, resulting in increase of blood pressure and consequently increased brain and heart perfusion, interrupting, terminating or at least alleviating the pathological condition.
3. Bronchospasm, laryngospasm, hiccup, epileptic seizures, and tremor in Parkinson's disease may be inhibited by impulses from the inspiratory centre via the reticular formation, transmitted through interneurons providing inhibitory influence to the relevant control centres in the brainstem and elsewhere.
4. In alternating hemiplegia, sleep paralysis and absence type epilepsy: stimulation via the inspiratory centre and interneurons activates the descending part of the reticular formation, which activates motoneurons, terminating, or at least alleviating the attack.
5. In comatose states, depression, insomnia, Alzheimers disease, anorexia nervosa, bulimia, and autism, stimulation via the inspiratory centre and interneurons influences the ascending part of the reticular formation. This inhibits or provides relief in depression, bulimia, anorexia nervosa and increases concentration and other cognitive functions. This improves some comatose states, may inhibit the development of Alzheimer's disease and autism and has a positive influence on insomnia and psychiatric disorders.

Resuscitating stimulation of the inspiratory neurons of the brainstem should be understood to mean stimulation of the human body such that the aspiration reflex or its alternatives are induced, which will influence various brainstem centres. Through such stimulation other parts of the brain relevant for the conditions treatable with the device are influenced. The aspiration reflex and its alternatives have as a common feature strong and short inspiratory efforts comparable to that occurring before or during one or more of gasp, sniff, sigh or augmented breath.

FIG. 1 shows a block diagram of a resuscitating device 10. The resuscitating device 10 has a casing 11. Enclosed in the casing 11 is a battery 13 which is connected to electronics 12. The battery 13 may comprise lithium iodine with nanocrystalline cathode components, as generally used in cardiac pacemakers. The electronics 12 are connected to a detection device 16 via suitable wires 14, as well as to a stimulation device 17 via suitable wires 15.

Figure 2:
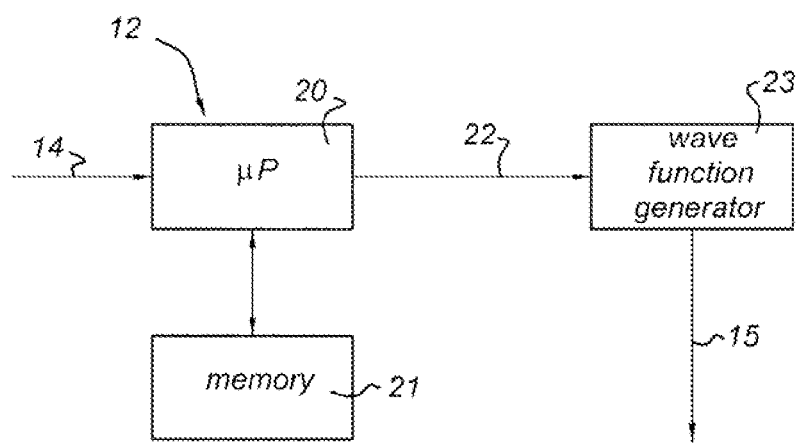
FIG. 2 shows an example of electronics that can be used in the present invention.

The electronics 12 may be implemented by means of an analogue circuit, a digital circuit or a computer arrangement with a processor instructed by a suitable computer program, or any combination thereof. FIG. 2 shows an embodiment based on a computer arrangement.

As shown in FIG. 2, the electronics 12 comprise a controller, e.g., in the form of a microprocessor 20 which is connected to a memory 21. Moreover, the microprocessor 20 is connected to a wave function generator 23 via suitable wires 22, which has an output connected to the wires 15 that are connectable to stimulation device 17.

The memory 21 may be implemented as several memory units of different types (RAM, ROM, etc.). The memory 21 stores instructions of a program to allow the microprocessor 20 to perform one or more functions. Optionally, memory 21 stores a number of detected parameter values as obtained from detection device 16. The memory 21 may be any suitable memory for storing a predetermined function such as a computer readable memory. The predetermined function may be a mathematical function or correlation. Suitable functions may be functions that are suitable for determining whether a determined parameter value is equal to, greater than or smaller than a predetermined threshold value. Based on his knowledge the skilled person will be able to determine suitable functions on the basis of which a response is required as a function of the determined parameter values. E.g. the function may relate the absence of certain parameter values below a certain threshold value to a certain time frame. Such a function may be determined to detect the absence of breathing during a certain time period e.g. 2 seconds and longer, 5 seconds and longer or 10 seconds and longer.

Based on the program as stored in the memory 21, the microprocessor 20 is able to process the number of detected parameter values as obtained from the detection device 16 in said function. For this, the detected parameter values are loaded into the microprocessor 20 either directly from the detection device 16 or alternatively from the memory 21 into which the detected parameter values were previously loaded. The function is loaded in the microprocessor 20 from the memory 21 or in an alternative embodiment the predetermined function may be embedded in said microprocessor 20. In the latter embodiment at least one memory is (partially) integrated in the microprocessor 20.

The detection device 16 may be any suitable device for detecting a number of parameter values. In the present specification, a "number" shall mean one or more unless explicitly stated otherwise. In use, the detection device 16 provides an output signal on wire 14, representing determined parameter values in response to determined parameter values. The determined parameter values are values of a parameter as measured/determined by the detection device 16 within a certain time frame. The parameter may be any parameter on the basis of which it may be determined whether a subject is in need of induction of autoresuscitation.

Parameters suitable for determining whether a subject is in need of resuscitation include but are not limited to parameters corresponding to muscle activity, parameters corresponding to breathing, or parameters corresponding to cerebral activity, such as electrical activity of neural cells including brain cells, or electrical activity recorded from the pharynx, the ear or any other suitable point on the body of a human being. Other sensors may be applied as well, like a sensor to measure body temperature, a sensor to measure pressure, and a sound sensor, like a microphone.

Parameters corresponding to muscle activity include but are not limited to movement and electrical activity of muscles. Movement of muscles may be detected by any detection device 16 suitable for detecting movement, such as a number of accelerometers. Electrical activity of muscles may be detected by use of any suitable device known in the art such as devices conventionally used for detecting an electromyogram (EMG), including an electrocardiogram (ECG), electroneurogram (ENG), actogram indicating contraction, etc. In one embodiment, the detection device 16 is arranged to record an electromyogram (EMG) detected by a detection electrode connected to the detection device 16. The detection electrode 16 may be suitable for attachment to the human diaphragm. The EMG data, including for instance intensity, frequency, repeatability of phasic activity, is processed in microprocessor 20.

Parameters corresponding to breathing, include but are not limited to parameters corresponding to activity of muscles involved in breathing activity such as the diaphragm, the intercostal muscles, musculus pectoralis, abdominal muscles, muscles of the upper and lower airways and other muscles involved. The parameters corresponding to muscle activity as discussed above are suitable. In an alternative embodiment of the device according to the invention, the parameter corresponding to breathing activity may comprise gas flow in the airways and/or in the vicinity of the inlets/outlets of the subject's airways. It must be understood that the inlets/outlets of the subject's airways comprise normally the nostrils and/or mouth or a tracheal tube in some patients. The skilled person will be familiar with suitable devices for determining gas flow, e.g. by a pneumotachograph or thermometer, such as a thermistor, Pt100, Pt1000 and other.

In a further alternative embodiment of the device 16, the parameters corresponding to breathing activity to be detected may comprise sound. During breathing sounds are created, for instance caused by air whirling in the larynx. Respiratory sounds include but are not limited to snoring, inspiratory and expiratory stridor, groaning, etc. These sounds may be used to detect breathing activity of a human being. Suitable detecting devices 16 for detecting sounds are microphones, a membrane connected to a coil/magnet system or any other device comprising a membrane with the possibility to register movement or displacement of this membrane. Such sounds may be detected in, for instance, at least one of the mouth, a nostril and an ear.

In a further alternative embodiment of the invention an electro encephalogram may be used by electronics 12. If so, detection device 16 is also arranged to detect electrical activity of the brainstem. Cerebral activity produces electrical fields which can be measured e.g. on the skin of the skull or the ear of a human being. Alternatively such signals may be recorded from the pharynx of a human being. Suitable devices for detecting electrical activity from the surface of the pharynx are conductive patches connected to a suitable amplifier and filter. The skilled person will be familiar with suitable devices for determining electrical activity of the brain from the skin.

Alternatively, the detection device 16 is connected to a sensor to measure oxygen saturation in the blood of the subject. Measuring oxygen saturation is a good indication of whether or not apnoea is present. In the context of the present invention this can advantageously be done within the nostril itself.

The stimulation device 17 is arranged to provide a response as a function of the number of processed parameter values. The stimulation device may comprise a number of stimulation units designed to provide resuscitating stimulation in order to stimulate and/or reactivate the inspiratory centre of the brainstem.

In accordance with the present invention a nose stimulator is used for resuscitating stimulation of the inspiratory centre of the brainstem. The nose stimulator is arranged to provide stimuli to one or more points on or near the nose where, by providing a suitable stimulation, an aspiration reflex will be induced. Such a point may, for instance, be acupuncture point GV26 of the nasal philtre.

Figure 4:
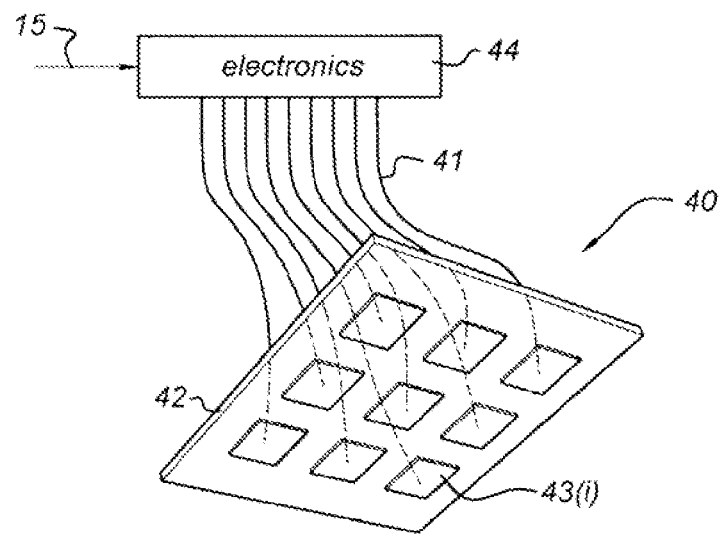
FIG. 4 shows a substrate with a matrix arrangement of stimulation units.

The stimulation device 17 may be a mechanical or an electrical stimulation device. The electrical stimulation device may include a separate power source. A suitable power source may be an array of charged capacitors, allowing voltage selection for the stimulation, in case spikes are used. This separate power source may, alternatively, be absent in which case the stimulation device 17 will be connected to the battery 13 within casing 11 via wiring 15. The wave generator 23 as shown in FIG. 4 may be part of the stimulation device 17. In combination with such a power source, the wave generator 23 is arranged to produce a desired control signal for the stimulation device 17, for instance in the form of block waves, sinus waves or spikes of different length, frequency and amplitude, or combinations thereof.

The stimulation device 17 may further include or be connected to one or more stimulation electrodes for delivering an electrical stimulation to one or more acupuncture points of the nose. Such electrodes receive suitable stimulation signals based on the control signal received from the electronics 12. Electrodes may be mono-polar or multipolar, including bipolar electrodes, and may be placed on the surface of the body or anchored in various tissues of the subject's body in, on or close to the nose. For stimulation of points on, in or near the nose, for instance on the nasal philtre, the electrodes may be placed on the skin. Between the electrode and the skin, a conducting gel or paste may be used. Alternatively electrodes may have the form of needles arranged to at least partially penetrate the subject's skin.

In an embodiment, the stimulation device 17 comprises a plurality of stimulation electrodes. By using a plurality of stimulation electrodes more complex stimulation currents can be provided to the body. This also provides the possibility of precise definition of the area to be stimulated. If a plurality of stimulation electrodes is used it is preferred that there is some distance between said electrodes. Due to this distance the electrical current will travel over that distance through the subject's body. This will enhance the stimulatory effect.

If spikes are used for the control signal, variations in the amplitude and duration of the spikes, i.e. the amount of energy can be made, apart from trains of spikes over an extended period of time (seconds)(Beňačka and Tomori, 1995). Sinus waves of various frequencies and duration, block waves, spikes, spike trains and any combination of these can be used. It is preferred to not just transfer energy, but to stimulate the targeted response centres more complexly to elicit the desired physiological response.

In an embodiment, the microprocessor 20 is designed to activate the wave function generator 23 if an EMG as detected by detection device 16 does not satisfy a predetermined criterion, such as a lack of normal EMG activity for >10 sec (central apnoea) or extremely strong EMG activity accompanied by stop of airflow (obstructive apnoea) as detected by detection device 16. Then, upon activation the wave function generator 23 may generate the control signal in the form of a predetermined wave, such as a sinus wave, block wave, spike train or any combination in a suitable frequency, duration and amplitude that is guided through electrical wires to its stimulation electrode.

Nose Stimulator.

Figure 3A:
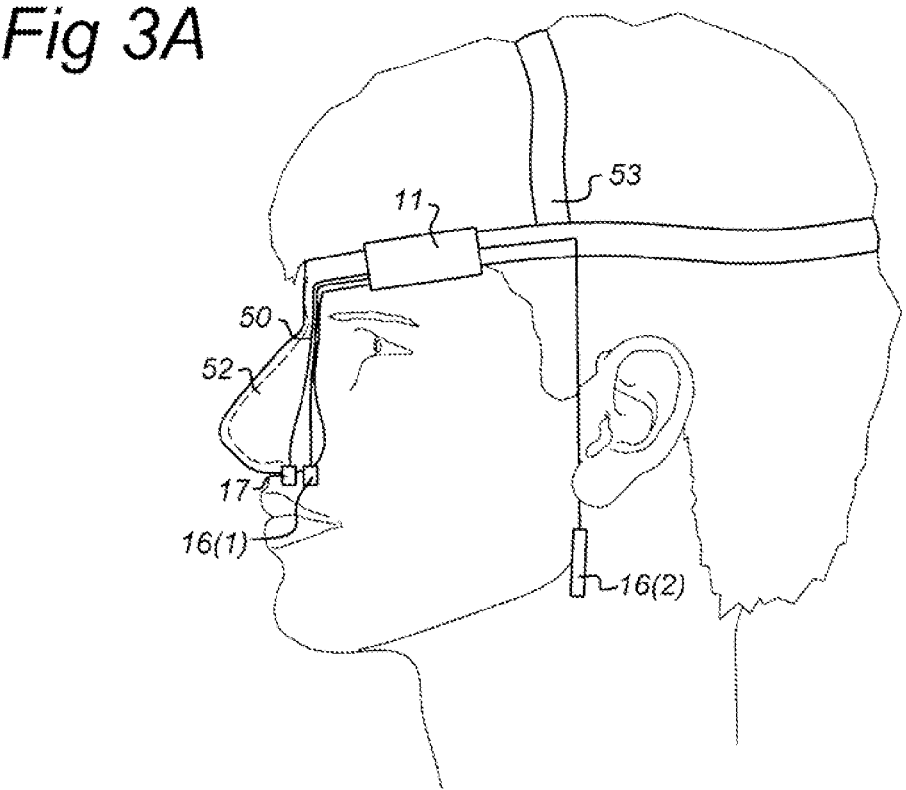
FIG. 3a shows a human head wearing a device according to the invention.

FIG. 3a shows an embodiment of a nose stimulator in accordance with the invention.

The nose stimulator as shown comprises the following features. The nose stimulator comprises a nose cap 52 that may be connected to one or more bands 53 that can be worn by a human head. Other supporting devices, like a hat or cap, can be used instead to fix the nose cap 52 to the human nose and prevent the nose cap from falling of the head. The nose cap 52 comprises a first detection device 16(1) which, in use, is located close to one or both of the nostrils and is arranged to sense airflow. Such an airflow sensor can be based on measuring temperature changes (e.g. via a thermistor), pressure changes, changes in airflow, sound, etc. Thus, detection device 16(1) is arranged to sense whether or not the human being is still breathing. The detection device 16(1) generates a breathing signal in dependence on the sensed airflow.

Although the nose stimulator is shown to be attachable to a human's nose by means of nose cap 52 the invention is not restricted to this embodiment. Any holding device arranged to attach at least the stimulator 17 of the nose stimulator to the nose may be used instead, including a nose plug, a piercing, screws, nails, bolts, a click system, rivets, staples and bayonets. Such a holding device can be attached to one of the nostrils or the nose bone or any other suitable part of the nose.

The detection device 16(1) is connected to casing 11 that accommodates electronics 12 and battery 13 (FIG. 1). It is arranged to send the breathing signal to the electronics 12. Transmission of this breathing signal can be done via a wire 50. However, a wireless connection can be used instead.

Casing 11 is shown to be connected to the band 53. However, casing 11 may be placed at any suitable location on the human body. In one embodiment, the casing 11 and its internal components are integrated in the nose cap 52. Detector 16(1) may be located in casing 11 too in such an embodiment.

Figure 3B:
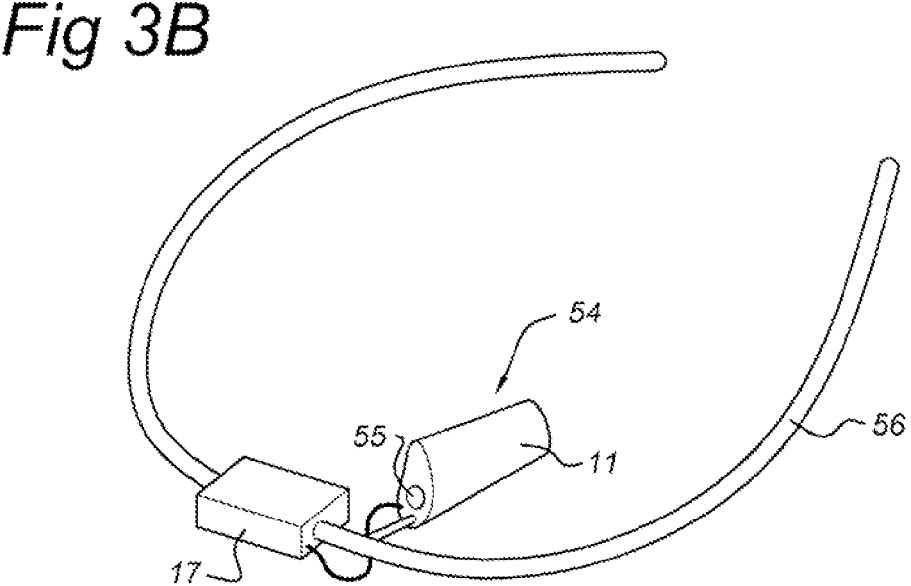
FIG. 3b shows an embodiment for providing stimuli to a nasal philtre.

FIG. 3b shows an embodiment with a nose plug 54 which can be inserted in a humans nose. The casing 11 is made from a flexible material and designed to adapt to the form of the nostril. The casing 11 is provided with a through hole 55 through which the human being can breath. A breathing sensor is integrated in the casing 11 and senses the airflow through the through hole 55. Such a sensor can be based on any physical principle indicative of breathing activity, like flow measurement, temperature measurement, pressure measurement, etc. Electronics 12 is also located within the casing 11.

Stimulation device 17 is connected to these electronics, e.g., by suitable wiring. Both the stimulation device 17 and the plug 54 can be connected to a brace or bracket 56 to be worn on a human head. When a user fits such a brace or bracket 56 on his/her head, the consequence will be that the plug 54 remains located in the nostril and the stimulation device 17 remains pressed against a predetermined portion of the nasal philtre. Also the other embodiments may be designed such that when the system is worn in or on the human nose the stimulation device 17 is pressed against a predetermined portion of the nasal philtre.

Casing 11 may also be connected to a second detection device 16(2). In the shown embodiment, the second detection device 16(2) is arranged to be fixed to the human skin close to the carotid in order to sense the heartbeat of the blood flow in the carotid. However, alternatively, the second detection device 16(2) can be located on any portion of the human body where the heartbeat can be sensed, as explained above. For instance, the heartbeat may be sensed in or close to the nose in which case both detection device 16(1) and detection device 16(2) may be accommodated in casing 11 and casing 11 can be integrated in nose cap 52.

In the embodiment of FIG. 3b, such a second detection device 16(2) may be part of the casing 11 or be integrated within one single housing with stimulation device 17.

The second detection device 16(2) transmits a heartbeat signal to the electronics 12 inside casing 11. Based on a suitable software program stored in memory 21, processor 20 can then generate a cardiogram using mathematical equations known to a person skilled in the art.

The processor 20, using a suitable program stored in memory 21, is arranged to determine whether the breathing signal as received from the first detection device 16(1) and the heartbeat signal received from the second detection device 16(2) indicate that the human being is suffering from apnoea. If so, the processor generates a suitable output signal for wave function generator 23 which, based on that output signal, will generate a suitable control signal for stimulation device 17.

The stimulator 17 is shown to be connected to electronics 12 via a wired connection. However, a wireless connection can be used instead. Like detection device 16(1) and detection device 16(2), stimulation device 17 may be accommodated in casing 11 and casing 11 can be integrated in nose cap 52. In the embodiment shown in FIG. 3b, casing 11 and stimulation device 17 may be physically integrated within one apparatus.

The stimulation device 17 is arranged to stimulate one or more points on the nasal philtre where an aspiration reflex may be induced, for instance acupuncture point GV26 of the nasal philtre.

In an embodiment, the stimulation device 17 is a mechanical stimulation device arranged to mechanically stimulate one or more such points on the nasal philtre. Mechanical stimulation means are means that are suitable for touching with an elastic nylon fibre and thin polyvinyl catheter, or providing pressure to selected parts of the ear. Mechanical stimulation may be also provided by means of gas pressure pulses. Other suitable devices for providing mechanical pressure comprise acupuncture, acupressure, electro-acupuncture electro-acupressure (combination of mechanical and electrical stimulation) devices.

Figure 7:
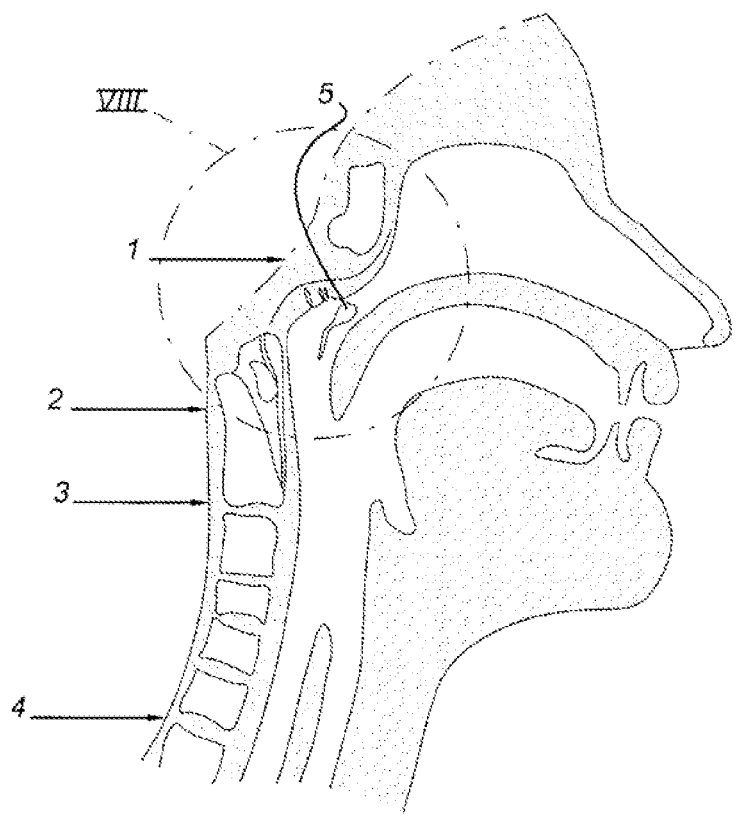
FIG. 7 is a schematic cross section of a part of the human head and neck.

In an embodiment, the stimulation device is arranged for delivering at least one of electrical, chemical or mechanical stimulation through one of the nostrils to the nasopharynx. As shown in FIG. 7 the pharynx of the human body is situated from the underside of the skull to the level of cervical vertebra C6. The pharynx may be divided in three compartments, the nasopharynx (roughly situated behind the nasal cavity between arrows 1 and 2), the oropharynx (roughly situated behind the oral cavity between arrows 2 and 3) and the laryngopharynx (roughly situated behind the larynx between arrows 3 and 4).

Figure 8:
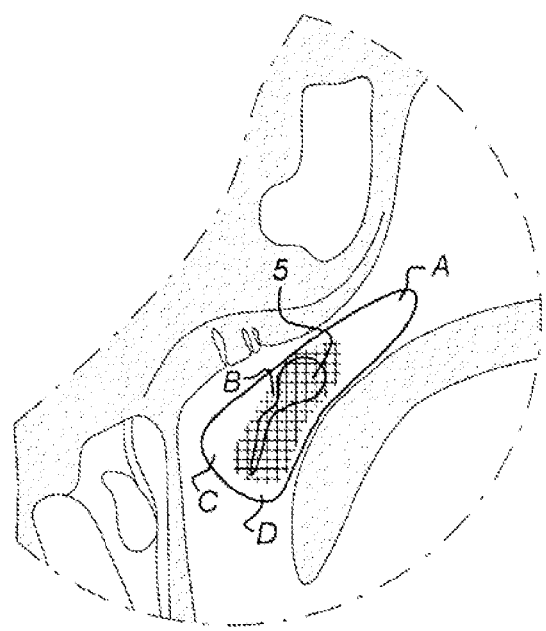
FIG. 8 is a detail from FIG. 7.

FIG. 8 shows a portion of FIG. 7 on an enlarged scale. Resuscitating stimulation may be administered via a nostril in the area of the nasopharynx enclosed by reference marks A, B, C, D surrounding the tuba auditiva 5. Resuscitating stimulation may be administered in the direct proximity of the tuba auditiva 5 itself indicated by the hatched lines in FIG. 8. Stimulation may, for instance, be provided via air pulses generated by a suitable air pulse generator through a hose inserted into the nostril. Alternatively, this can be done via a solid, flexible thread connected to a suitable motor and touching the nasopharynx, which motor provides the thread with a suitable mechanical impulse. Electrical stimulation may, alternatively, be provided through a conducting wire.

Figure 3C:
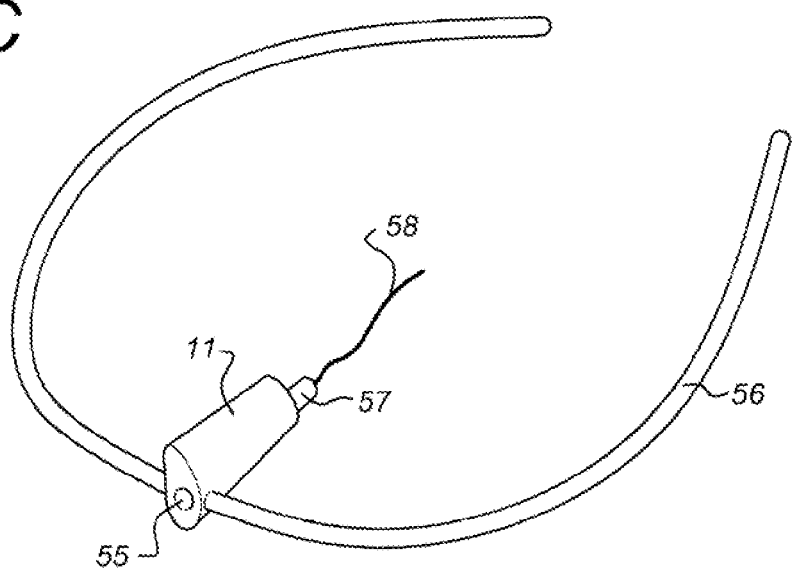
FIG. 3c shows an embodiment for providing stimuli to a nasopharyngeal area.

FIG. 3*c* shows an embodiment for providing stimuli to the nasopharyngeal area. The embodiment of figure comprises casing 11 in the form of nose plug. The casing 11 is connected to brace/bracket 56 to be worn on a human head and arranged for clamping the casing 11 inside the nostril when it is in use. The casing 11 has through hole 55 such that a human being when having the nose plug inserted in his/her nostril can breath through the nostril. A small tube 57 extends from the rear side of the casing. A thread, wire or fibre 58 extends through the tube 57, which is connected to a suitable motor (not shown) and arranged to stimulate the nasopharyngeal area by a suitable mechanical movement as instructed by electronics 12. Alternatively, the wire 58 may be connected to electronics 44 within stimulation device 17 arranged to provide electrical stimulation signals to the wire 58 as instructed by electronics 12.

In an embodiment, the nose stimulator comprises a stimulation matrix. FIG. 4 shows a stimulation matrix 40. The stimulation matrix 40 is part of or connected to the stimulation device 17. As shown in FIG. 4, the stimulation matrix 40 has a substrate 42 provided with a plurality of stimulation units 43($i$), i=1, 2, 3, . . . , I. The stimulation units are arranged in a matrix form. The arrangement shown comprises stimulation units 43($i$) in a regular matrix pattern. However, the embodiment is not restricted to this arrangement. Irregular patterns may be used instead. In this embodiment the stimulation units 43($i$) are arranged in a two dimensional pattern.

In an embodiment, the stimulation units are stimulation electrodes 43($i$) for delivering an electrical stimulation to the nose or an area close to the nose. Such electrodes 43($i$) receive suitable stimulation signals via wires 41 from electronics 44 within stimulation device 17 based on the control signal received from the electronics 12 via wire 15. Electrodes 43($i$) may be mono-polar or multipolar, including bipolar electrodes. For stimulation of acupuncture points on the nose, for instance on the nasal philtre, the electrodes 43($i$) may be placed on the skin. Conducting gel or paste may be used as a conducting medium between the skin and the electrode. Alternatively, electrodes 43($i$) may have the form of needles arranged to at least partially penetrate the subject's skin.

By using a plurality of stimulation electrodes 43($i$) arranged in the form of a two dimensional matrix more complex stimulation currents can be provided to the ear. This also provides the possibility of precise definition of the area to be stimulated. There is some distance between the electrodes 43($i$). Due to this distance the electrical current will travel over that distance through the subject's ear. This will enhance the stimulatory effect.

If spikes are used for the control signal, variations in the amplitude and duration of the spikes, i.e. the amount of energy can be made, apart from trains of spikes over an extended period of time (seconds)(Beňačka and Tomori, 1995). Sinus waves of various frequencies and duration, block waves, spikes, spike trains and any combination of these can be used. It is preferred to not just transfer energy, but to stimulate the targeted response centres more complexly to elicit the desired physiological response.

Figure 9A:
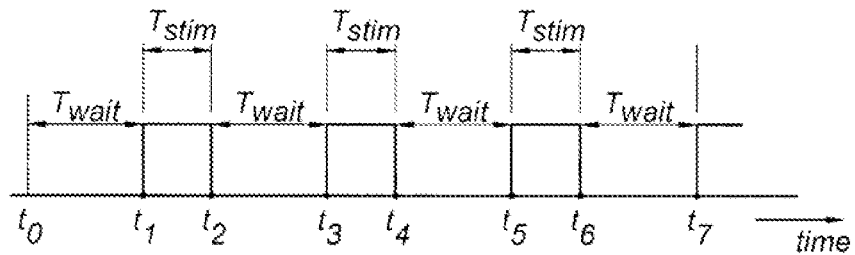
FIGS. 9a and 9b show examples of stimulation signals.

FIG. 9*a* shows a stimulation signal as generated by stimulation device 17 when the electronics 12 detect that a person is in a state of developing apnoea. At time $t_0$ electronics 12 determine that the person concerned was breathing such as to have a high risk of developing apnoea. The combination of electronics 12 and stimulation device 17 is arranged such that a first stimulation signal is only generated at a time $t_1$ after a first delay time $T_{wait}$. As shown in FIG. 9*a*, the first stimulation signal may have the form of a spike, pulse or wave train which lasts a predetermined time $T_{stim}$ until time $t_2$. If breathing has not started as a result of the first stimulus a second stimulation signal is generated at time $t_3$ after waiting time $T_{wait}$. Again, the stimulation signal lasts a time $T_{stim}$ until time $t_4$. A third second stimulation signal is generated at time $t_5$ after waiting time $T_{wait}$. Again, the stimulation signal lasts a time $T_{stim}$ until time $t_6$. Etc.

During the time the stimulation device 17 is generating the stimulation signal as shown in FIG. 9*a*, the electronics may, at any time interrupt the stimulation device 17 and cause stimulation device 17 to stop once the electronics 12 have determined that the person concerned has returned to breathing. The pattern shown in FIG. 9*a* may be generated by stimulation device 17 automatically once it has received a trigger signal from electronics 12 and may continue until it receives such an interrupt signal. Alternatively, electronics 12 may be arranged to control generating every stimulation pulse one-by-one.

In accordance with the present invention, the combination of electronics 12 and stimulation device 17 may be arranged to vary the waiting time $T_{wait}$ between consecutive stimulation pulses. It has been found that a suitable waiting time $T_{wait}$ may vary between 0 and 10 seconds, preferably between 0 and 5 sec, more preferably between 0.5 and 2 sec. Moreover, tests have shown that the stimulation time $T_{stim}$ may vary between 0 and 10 seconds, preferably between 0 and 5 sec, more preferably between 0.5 and 2 seconds. Especially the first waiting time $T_{wait}$ may deviate from the other waiting times between consecutive stimulation pulses cf. for instance FIGS. 11*a* and 11*b*.

It is observed that the same tests have also shown that if a person does not continue breathing within 10 seconds after cessation of breathing but later, that applying the stimulation pattern leads to shortening the apnoea episodes.

It is observed that the same tests have also shown that if a person does not continue breathing within 10 seconds after cessation of breathing but later, that applying the stimulation pattern as shown in FIG. 9a results in the person having the feeling that he has been sleeping better then normally.

Figure 9B:
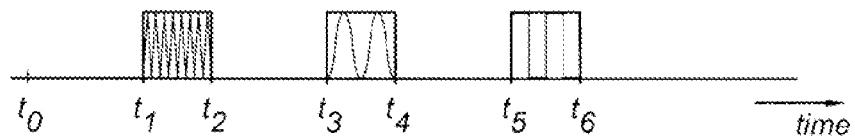

FIG. 9b shows that the actual stimulation signal within the pulse shaped pattern of FIG. 9a may have any desired form, i.e., a triangle form, a sinusoidal form, a block form, etc. Tests have shown that the average repetition frequency of the stimulation signal within the stimulation pulses may be between 1 and 500 Hz. Successful results as to counteracting apnoea have been shown with an average repetition frequency of about 8 and 60 Hz. A preferred range is therefore 1 to 100 Hz.

In an embodiment, the stimulation units 43(i) are mechanical stimulation units arranged to provide a mechanical stimulus to the human body. Such mechanical stimulation units 43(i) may be formed by electrostriction components which produce a mechanical movement when excited by an electrical current. Such mechanical stimulation units 43(i) may have the form of needles.

Figure 5:
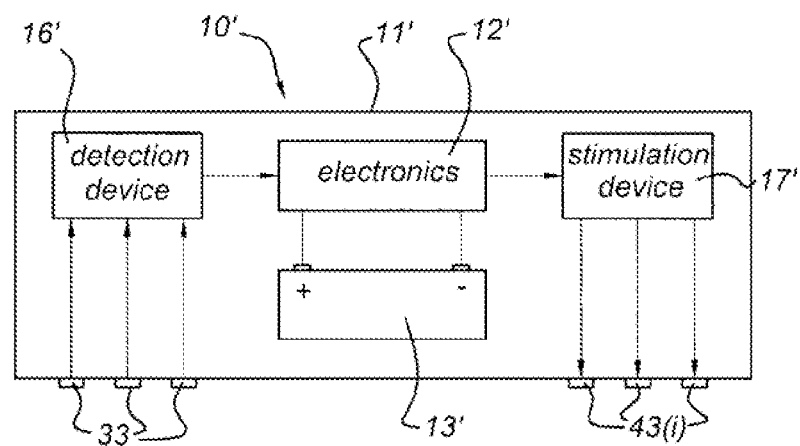
FIG. 5 shows an alternative arrangement of the arrangement of FIG. 1.

As observed above, the device 10 according to the invention may be designed such that it does not comprise any external detection or stimulation leads. As shown in FIG. 5, the casing 11 of such a device 10, then, accommodates for instance the detection devices 16(2), electronics 12, battery 13 and stimulation device 17. The battery 13 is shown to be connected to the electronics 12 but may equally well be connected to the detection devices 16(1)/16(2) and the stimulation device 17. Detection device 16(1) is shown to be located outside the casing 11 for sensing an airflow through one of the nostrils.

Then, the casing 11 may be partly conductive. For instance, the casing 11 may be provided with conductive pads 33 connected to the detection device 16(2) and operating as an antenna to detect the heartbeat of the human body.

The conductive casing 11 may similarly be provided with the stimulation units 43(i) connected to the stimulation device 17 which are used to guide an electric stimulation current to a part of the human body on the nasal philtre.

Casing 11 may be made from a conducting material like titan or platina. In such a case, when the stimulation units 43(i) themselves are conductive too they should be electrically isolated from the conductive casing 11'. This can be done in any way known to a person skilled in the art.

In one embodiment, the casing 11 that accommodates electronics 12 and battery 13 is made of a flexible material. A suitable material is silicone since that is found to be well tolerated by the human body. However, other flexible biocompatible materials tolerated by the human body may be used instead. The casing 11 can be an integral part of nose cap 52 such that they are both flexible and can easily adapt to different noses of different people. Making the casing 11 from a flexible biocompatible material is especially advantageous in the embodiment of FIG. 3b. This is also true for the embodiment of FIG. 3b in which the stimulation device 17 is an integral part of casing 11.

Figure 6:
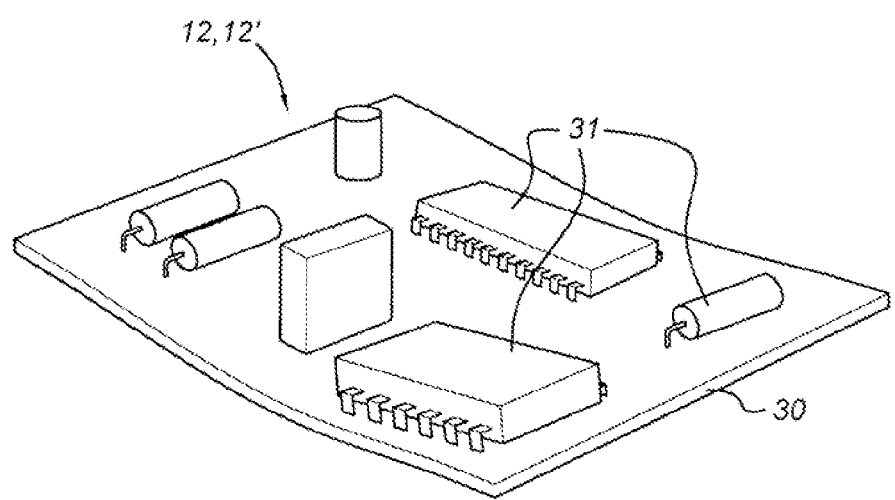
FIG. 6 shows a flexible substrate provided with electronic components.

In such an embodiment, the battery 13 may be made flexible too. Alternatively, many small batteries may be joined to form a virtually flexible battery pack. The electronics 12 may be made of flexible components as well or at least electronic components may be provided on a flexible substrate, e.g., a flexible printed circuit board. FIG. 6 shows such a flexible substrate 30 having electronic components 31 located on at least one surface. As shown in FIG. 5, the stimulation device 17 may be located inside the casing 11 too and be made of electronic components on a flexible substrate too. Then, the stimulation device 17 may be arranged as shown in FIG. 6 as well. The electronic components of the electronics 12 may be arranged on a first flexible substrate and the stimulation device 17 may be arranged on a second flexible substrate. However, these first and second substrates may be a single substrate. The battery 13 may be provided on that substrate too. As also shown in FIG. 5, the detection device 16' may be located inside the casing 11' too and be made of electronic components on a third flexible substrate too. Then, the detection device 16' may be arranged as shown in FIG. 6 as well. The substrates with the electronic components of the electronics 12', the detection device 16' and the stimulation device 17' may be separate substrates. Alternatively, however, they may be one single substrate.

Figure 10:
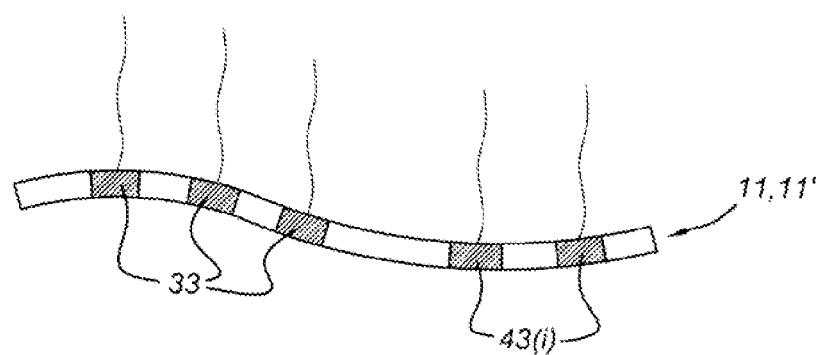
FIG. 10 shows a portion of a flexible casing with sensors and stimulation electrodes.

In the embodiment where the casing is made of silicone and the stimulation units are stimulation electrodes 43(i), these stimulation electrodes 43(i) can be made as electrically conductive silicone portions in the silicone casing 11, 11'. This can be done by providing silicone portions of the casing 11, 11' with doping materials like titan or platina Such an embodiment is shown in FIG. 10. FIG. 10 shows a portion of a cross section of the flexible casing 11, 11' with sensors 33 and stimulation electrodes 43(i). In this embodiment, both the casing 11, 11' and the sensors 33 and the stimulations electrodes 43(i) are made of silicone. They are all produced from a silicone substrate in which predetermined portions are doped with a suitable doping material like titan or platina to become sensors 33 and stimulation electrodes 43(i).

Suitable conductive wirings are connected to these latter portions for electrically connecting the sensors 33 to the detection device 16, 16' and the stimulation electrodes 43(i) to the stimulation device 17, 17'.

Such a device can be made auto-optimizing. The electronics 12, 12' can be arranged to perform a feedback measurement, such that stimulation can be performed at a point where the aspiration reflex can be elicited best. In one embodiment the electronics will, through a suitable sensor, register the strength of the aspiration reflex; this can for example be performed by measuring airflow through the nose or mouth, measuring sound, heart rate, blood pressure etc. Impedance of the stimulation point may be a guide for finding the optimal point. In this case the device may use impedance measurement to find suitable points for stimulation.

The electronics 12, 12' can be arranged to send different types of stimulation signals to the stimulation units 43(i), either in form or in amplitude or both. The effect of the different stimulation signals per stimulation unit 43(i) can be measured by detection devices 16(1), 16(2) and be evaluated by electronics 12. Electronics 12 can be programmed to amend these stimulation signals by amending its control signal as output to the stimulation device 17.

Moreover, the electronics 12 can be programmed to randomly vary its generated control signal such that the stimulation signals produce random stimuli over the area of the nose stimulated by the stimulation units 43(i). This could reduce adaptation of the body to the generated stimuli and, thus, enhance efficiency of the device 10.

The electronics 12 can be programmed to evaluate the breathing signal as received from the detection device 16(1) and to detect any breathing disturbance, e.g., occurrence of hyperventilation. Then, based on this evaluation, electronics 12, 12' can produce a suitable control signal to the stimulation device 17 such that the stimulation device 17 produces suitable stimuli to the nose in order to counteract the breathing disturbance.

Figure 11A:
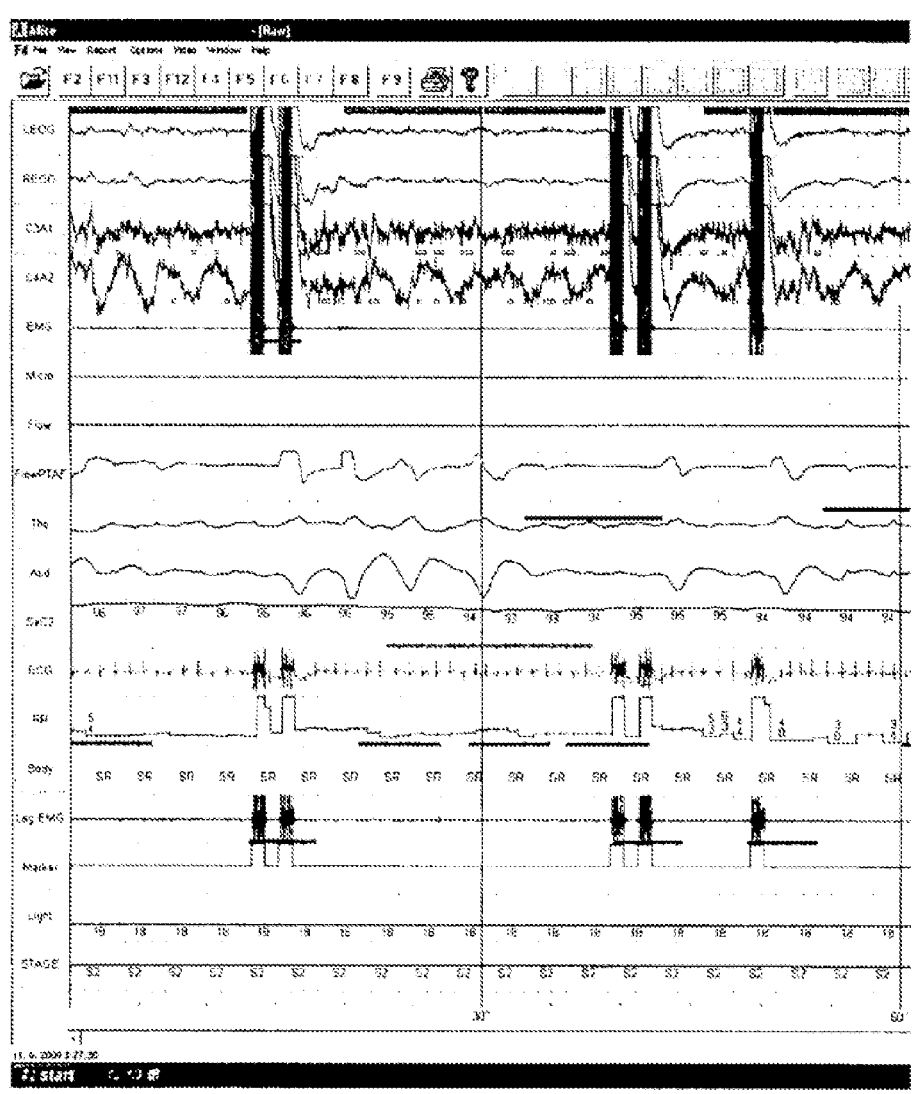
FIGS. 11a and 11b show some experimental results.
Figure 11B:

FIGS. 11a and 11b show some experimental results of providing stimulation to an auricle of a person suffering from sleep apnoea. The explanation to the parameters shown is as follows:

LEOG, REOG: Left and Right Electro OculoGram, respectively,
C3A1, C4A2: signals which are a measure of EEG,
EMG: Electro Myogram
FlowPTAF: breathing signal,
Tho: thorax movement
Abd: abdominal movement
Sao2: oxygen saturation
ECG: electrocardiogram
RR: heart rate
Leg EMG: Electro Myogram as measured on a leg
Marker: when high indicating a stimulation, when low indicating no stimulation.

FIGS. 11a and 11b show the following settings. 4 seconds after the apparatus has determined that the subject has stopped breathing or has started shallow breathing, the apparatus generated a stimulation signal to the nasal philter. The stimulation lasted 1 second. The stimulation signal itself had a frequency of 8 Hz. The time separating two consecutive stimuli was also 1 second. So, $t_1-t_0=4$ seconds, $t_{stim}=1$ second and $t_{wait}=1$ second.

In FIGS. 11a and 11b the marker channel shows when a stimulation is addressed. As a consequence of this electric stimulation artefacts are shown in various electrically derived channels. In all cases breathing is resumed as a result of one or more stimulations, as is shown in the flowPTAF channel.

The method according to the invention is suitable for the treatment of one or more of but not limited to apnoea, such as central apnoea, obstructive apnoea or mixed type apnoea, transient ischemic attacks (TIA), hypotension, syncope, haemorhagic shock (loss of blood), bronchospasm, laryngospasm, hiccup, tremor associated with Parkinson's disease, epileptic seizure, absence type epilepsy, migraine, alternating hemiplegia, Alzheimers disease, depression, anorexia nervosa, bulimia, autism, psychiatric disorders, insomnia, sleep paralysis, comatose states. As used in this specification the term treatment should be construed to encompass alleviation of discomfort or provide reversal of life threatening functional disorders.

It should be understood that the embodiments presented in the examples above are solely intended to illustrate the present invention and are not intended to limit the scope of the invention which is only limited by the annexed claims and its technical equivalents.

REFERENCES

Arita H., Oshima T., Kita I., Sakamoto M.: Generation of hiccup by electrical stimulation in medulla of cats. Neurosci. Lett. 175: 67-70, 1994.
Batsel H. L., Lines A. J.: Bulbar respiratory neurons participating in the sniff reflex in the cat, J. Exper. Neurol 39:469-481, 1973'
R. Beňačka, Disorders of central regulation of breathing and their influencing by upper airway reflexes (in Slovak). Orbis Medince S; No.: 53-63, 2004,
R. Beňačka and Z. Tomori, The sniff-like aspiration reflex evoked by electrical stimulation of the nasopharynx, Respir. Physiol. 102: 163-174, 1995.
J. Jakůs, Z. Tomori and A. Stransky, Neural determinants of breathing, coughing and related motor behaviours, Monograph, Wist, Martin, 2004.
Sridhar R., Thach B. T. et al.: Characterization of successful and failed autoresuscitation in human infants including those dying of SIDS. Pediatr. Pulmon. 36:113-122, 2003.
St John W. M., Bledsoe T. A., Sokol H. W: Identification of medullary loci critical for neurogenesis of gasping J. Appl. Physiol. 56: 1008-1019, 1984.
Z. Tomori, M. Kurpas, V. Doni. and R. BeÁa.ka, Reflex reversal of apnoeic episodes by electrical stimulation of upper airway in cats, Respir. Physiol. 102: 175-185, 1995.
Z. Tomori, R. Beňačka, V. Doni. and J. Jakůs, Contribution of upper airway reflexes to apnoea reversal, arousal, and resuscitation, Monaldi Arch. Chest Dis. 55: 398-403, 2000.
Z. Tomori, R. Beňača and V. Doni., Mechanisms and clinico-physiological implications of the sniff- and gasp-like aspiration reflex, Respir. Physiol. 114: 83-98, 1998.
Z. Tomori and J. G. Widdicombe, Muscular, bronchomotor and cardiovascular reflexes elicited by mechanical stimulation of the respiratory tract, J. Physiol 200: 25-49, 1969.
Xie J., Weil M. H., Sun S., Yu T., Yang W.: Spontaneous gasping generates cardiac output during cardiac arrest, Crit. Care Med. 32: 238-240, 2004.

The invention claimed is:

1. An electronic stimulation system arranged to be worn in or on a human nose comprising:
   a casing;
   a first detection device arranged to sense at least breathing activity from a human being and to generate a detection signal accordingly,
   electronics arranged within said casing and comprising a controller connected to said first detection device and arranged to process said detection signal and to generate a control signal when said controller has determined that said human being is in a state of developing apnoea;
   a stimulation device arranged to receive said control signal from said electronics and to provide electrical stimuli;
   wherein said electronic stimulation system comprises a holding device arranged to attach at least the stimulation device to the nose, the holding device comprising either a nose cap having a form of a human nose and made of a flexible material or a nose plug made of a flexible material and designed to adapt to the form of a human nostril, and said electronic stimulation system being either arranged such that, when worn in or on said human nose, said stimulation device is pressed against a predetermined portion of the nasal philtre in order to provide said electrical stimuli to said predetermined portion of said nasal philtre or arranged to comprise a wire connected to said electronics in order to provide said electrical stimuli to a human nasopharynx, the stimulation device being arranged to generate a plurality of stimulation signals upon receiving said control signal from said electronics during a plurality of stimulation times $T_{stim}$, a first stimulation time only starting after a first waiting time after said electronics have established that said human has a high risk of developing apnoea, consecutive stimulation times being separated by a second waiting time, a consecutive stimulation time starting after said second waiting time, if the electronics have established that breathing has not started as a result of stimulation signals in a preceding stimulation time, wherein the first and second waiting times may be different and the stimulation signals having an average repetition frequency of 1 to 100 Hz, such as to provoke an induced aspiration reflex by a resuscitating stimulation of the respiratory area of the human brain stem, the first and second waiting time being between 0 and 10 seconds and the stimulation time being between 0 and 10 seconds.

2. The electronic stimulation system according to claim 1, wherein the casing is designed as said nose plug to be inserted in a nostril, the casing comprising said detection device and said stimulation device, the system comprising one of a thread, a wire and a fibre extending from the casing and arranged to stimulate a nasopharyngeal area.

3. The electronic stimulation system according to claim 2, wherein said casing is connected to one of a brace and bracket to clamp said casing in said nostril when said system is in use.

4. The electronic stimulation system according to claim 1, wherein the system comprises a second detection device arranged to sense a heartbeat of the human being, to generate a heartbeat signal to that effect and to transmit said heartbeat signal to said electronics, the electronics being arranged to generate said control signal in dependence on said heartbeat signal too.

5. The electronic stimulation system according to claim 4, wherein said second detection device is arranged to sense the heartbeat in at least one of a human carotid, vein and artery.

6. The electronic stimulation system according to claim 4, wherein said second detection device is arranged to generate the heartbeat signal from a portion of a human body in, on or near the nose.

7. The electronic system according to claim 1, wherein the system comprises a second detection device arranged to sense electrical signals from the brain of the human being and to generate an electro encephalogram (EEG) signal from the electrical signals, the electronics being arranged to generate said control signal also in dependence on said electro encephalogram signal.

8. The electronic stimulation system according to claim 1, wherein the first detection device is arranged to sense airflow caused by breathing through the nose or the mouth.

9. The electronic stimulation system according to claim 1, wherein said casing is made from a flexible material, selected from a series of flexible materials including silicone.

10. The electronic stimulation system according to claim 1, wherein the electronic stimulation system comprises a plurality of stimulation units arranged in a two dimensional matrix form.

11. The electronic stimulation system according to claim 10, wherein the stimulation units are either arranged as at least one of electrical stimulation units and mechanical stimulation units.

12. The electronic system according to claim 1, wherein the plurality of stimulation signals each have a form of one of a plurality of pulses, a plurality of triangular signals, a plurality of sinusoidal signals, a plurality of block signals.

13. The electronic stimulation system according to claim 1, wherein at least one of the first waiting time, the second waiting time and stimulation time is variable.

14. The electronic system according to claim 1, wherein the system comprises a sensor to measure oxygen saturation in the blood of the subject within a nostril.

15. The electronic system according to claim 1, wherein the waiting time is between 0 and 5 seconds.

16. The electronic system according to claim 1, wherein the waiting time is between 0.5 and 2 seconds.

17. The electronic system according to claim 1, wherein the stimulation time is between 0 and 5 seconds.

18. The electronic system according to claim 1, wherein the stimulation time is between 0.5 and 2 seconds.

19. A method of providing stimuli to a human body comprising;
providing an electronic stimulation system comprising a casing, a detection device, electronics arranged within said casing and comprising a controller connected to said detection device, a stimulation device, and a holding device arranged to attach at least the stimulation device to a nose of said human body, the holding device comprising either a nose cap having a form of a human nose and made of a flexible material or a nose plug made of a flexible material and designed to adapt to the form of a human nostril,
by said detection device, detecting at least breathing activity from a human being and generating a detection signal accordingly,
by said controller, processing said detection signal and generating a control signal when said human being is in a state of developing apnoea;
by said stimulation device, receiving said control signal and providing stimuli to at least one of a predetermined portion of a nasal philtre and a human nasopharynx;
by said stimulation device, providing said stimuli to at least one of the nasal philtre and the human nasopharynx, generating a plurality of stimulation signals upon receiving said control signal from said electronics during a plurality of stimulation times $T_{stim}$, a first stimulation time only starting after a first waiting time after said controller has established that said human has a high risk of developing apnoea, consecutive stimulation times being separated by a second waiting time, a consecutive stimulation time starting after said second waiting time if said electronics have established that breathing has not started as a result of stimulation signals in a preceding stimulation time, wherein the first and second waiting times may be different and the stimulation signals have an average repetition frequency of 1 to 100 Hz, such as to provoke an induced aspiration reflex by a resuscitating stimulation of the respiratory area of the human brain stem, the first and second waiting time being between 0 and 10 seconds and the stimulation time being between 0 and 10 seconds.

* * * * *